United States Patent [19]

Brown, Jr. et al.

[11] 4,431,508
[45] Feb. 14, 1984

[54] SOLID STATE GRAPHITE ELECTRODE

[76] Inventors: Harold M. Brown, Jr., 1125 Alpine Pl., Salt Lake City, Utah 84105; Jeffrey D. Owen, 136 U St., Salt Lake City, Utah 84103

[21] Appl. No.: 432,651

[22] Filed: Dec. 10, 1982

[51] Int. Cl.$^3$ .......................................... G01M 27/26
[52] U.S. Cl. ..................... 204/418; 204/416; 204/400
[58] Field of Search ............... 204/400, 415, 416, 418, 204/420

[56] References Cited

U.S. PATENT DOCUMENTS 4,214,968  7/1980  Battaglia .......................... 204/435

OTHER PUBLICATIONS

Anal. Chem. 54, 322-324 (1982).

Primary Examiner—John F. Niebling
Attorney, Agent, or Firm—Mallinckrodt, Mallinckrodt, Russell & Osburn

[57] ABSTRACT

A solid state graphite electrode to determine the activity of an ion-specie in solution. The graphite electrode of the present invention can be adapted for use as either an external reference electrode, an ion-selective electrode or as an internal reference electrode. The electrode includes, as an electrically conductive element, a supported section of graphite that is appropriately electrically connectd through a potentiometer to show a difference in ion concentration as a voltage potential or emf. One graphite surface for immersion in a test solution is hydrophobized by coating it with a solution that contains an organic liquid molecule to covalently bond with hydroxyl groups (OH) of the graphite surface, rendering that surface hydrophobic. Preferably, the organic liquid is a silanizing agent, which coating after drying is covered with a hydrophobic layer or membrane that is preferably a polyvinylchloride (PVC) plastic. For an ion-selective electrode, an ion sensor for the ion to be sensed is mixed in the membrane material coated over the hydrophobized graphite and in another embodiment for an internal reference electrode, a hydrophilic membrane containing pairs of a same chemical specie in differing oxidation states or redox couple can be sandwiched therebetween.

31 Claims, 9 Drawing Figures

Measurement of 10-3 M Ca$^2$ with a Silanized Graphite Internal Reference Electrode Coated with t-HDOPP in PVC versus four Differently Treated Graphite External Electrodes

SOLID STATE GRAPHITE ELECTRODE

BACKGROUND OF THE INVENTION

1. Field of the Invention

This invention relates to electrodes for use in measuring an ionic specie concentration. More specifically, this invention relates to a chemically treated graphite electrode that is suitable for use as an external reference electrode, that can be modified as an internal reference electrode for use in an ion-selective electrode.

2. Prior Art

To measure the concentration, or more correctly, the activity of an ion, an ion-selective electrode and an external reference electrode are utilized. A voltage potential or emf developed between these two electrodes can be detected with a potentiometric device. A change in potential between the electrodes will be proportional to the logarithm of the activity of the ion, as described by the well-known Nikolski-Eisenman equation.

The construction of an ion-selective electrode (ISE) in the past has involved an electrode body, usually consisting of a glass or plastic tube. Such electrode body has been filled with an aqueous reference electrolyte solution, for example, calcium chloride for a calcium ISE. In contact with the reference solution at one end, is a reversible half-cell that consists of a silver wire coated with silver chloride. The other end of the electrode body also in contact with the reference solution is covered with an ion-selective membrane. Examples of these types of electrodes are shown in U.S. Pat. Nos. 3,598,713; 3,502,560; 3,562,129; 3,691,047 and 3,753,887. A U.S. Pat. No. 4,214,968 dated July 29, 1980, to Battaglia, et al., summarizes the disadvantages of these types of ion-selective electrodes; for example, high cost, low durability and poor reproducibility.

Attempts to overcome the above shortcomings led to the "coated wire" ion-selective electrode illustrated in an article by Cattrall, R. W., and Frieser, H., *Analytical Chemistry* 43: 1905 and 1906 (1971). This electrode consisted of a platinum wire coated at one end with a layer of an ion-sensor mixed in polyvinylchloride (PVC). This type of electrode does not contain a defined internal reference electrode or an internal reference solution. Although simple and inexpensive, such an electrode drifts, needs frequent recalibration and is commercially unattractive, as set out in the Battaglia, et al patent, U.S. Pat. No. 4,214,968.

A hybrid reference electrode that incorporates features of a conventional liquid junction electrode and the coated wire electrode was developed by Ruzicka and Lamm, U.S. Pat. No. 3,926,764, dated Dec. 16, 1975. This electrode, rather than using a metal wire as the conductor, utilized a mixture of powdered carbon and teflon pressed or sintered together to form a solid conducting hydrophobic substrate. Embedded in one end of the teflon/graphite substrate was an "electrochemically reversible" redox system such as calomel ($Hg/HgCl_2$). The redox paste was in contact with a humid (10% $H_2O$) layer of water-soluble salt, such as $CaCl_2$ for the $Ca^{2+}$ ion-selective electrode. In some cases, as described in an article by J. Ruzicka, E. H. Hansen, J. Tjell *Analytical Chimica Acta* 67: 155–178 (1973), the water-soluble electrolyte is included in the calomel paste as $CaSO_4$. When the above system is coated with a hydrophobic membrane, for example a PVC membrane containing an ion-exchanger or carrier appropriate for a particular ion the electrode will constitute an ion sensitive electrode. Electrodes of this type generally drift only about 5 mV/day, according to Hulanicki and Trojanowicz *Analytica Chimica Acta* 87: 411–417 (1976). As such, they represent a real improvement over "virgin" graphite internal reference electrodes which are not hydrophobized and do not contain an electrically reversible redox system as described by Ansaldi, A. and Epstein, S., *Analytical Chemistry* 45: 595–596 (1973); the "virgin" graphite electrodes typically drift 600 mV/Day as set out in Fleet, B., Bound, G. P. and Sandbach, D. R. *Bioelectrochemistry Bioenergetics* 3: 158–168 (1976).

It is noteworthy that there was no substantial difference in drift when the calomel paste and dissociable salt was omitted from the teflon/graphite electrode, as set out in FIG. 1 of A. Hulanicki and M. Trojanowicz, *Analytica Chimica Acta* 87: 411–417 (1976). The significance of the observation was not noted in this work or in any subsequent work to the knowledge of the present inventors prior to the present application. This is evidenced by the considerable efforts by inventors to stabilize electrode drift by establishing an electrochemically defined reference junction. One such effort was to apply a hydrophilic gel to the conducting substrate (metal) to form a "solid-state electrode", as shown in U.S. Pat. No. 3,833,495, by Grubb dated Sept. 3, 1974 and U.S. Pat. No. 3,671,414, dated June 20, 1972; a French Pat. No. 2,158,905, dated June 15, 1973 and a patent by Genshaw, et al., U.S. Pat. No. 3,856,649, dated Dec. 24, 1974. The major drawback of this type of electrode is that it must be preconditioned by a technique that hydrates the electrode or else the electrode will yield non-Nernstian responses and drift substantially, as disccused in the Battaglia, et al. patent U.S. Pat. No. 4,214,968. Also, these electrodes tend to become inoperative after a short time since the membranes blister or swell as described by B. Fleet, G. P. Bound and D. Sandbach. *Bioelectrochemistry and Bioenergetics* 3: 158–168 (1976).

An attempt to correct the problems inherent in a hydrated gel internal reference electrode is shown in the Battaglia et al. patent. In this patent, the gelled internal reference solution is "dried" prior to application of the ion-sensitive membrane, resulting in "instant" working electrodes requiring no preconditioning:

" . . . the drift exhibited by these electrodes although sometimes substantial, can be calibrated to provide accurate and reproducible determinations of the concentration of specific ions in test solutions"

FIG. 3 of the Battaglia et al. patent shows drifts at the rate of about 60 mV/hr. This patent provides two general types of configurations for the electrode, as shown in FIGS. 1 and 2, and in example 2 therein, that use carbon as the conductive layer in contact with a redox couple layer.

The above cited patents all teach that, in order to obtain stable reference electrode systems, an electrochemically defined reversible system is required in contact with a conducting substrate, especially if that substrate is carbon or graphite. The literature emphasizes that carbon by itself displays considerable drift B. Fleet, G. P. Bound and D. Sanbach, 1976. Even though prior patents and the scientific literature have focused on the chemically defined redox system, it has been observed, as set out hereinabove, Hulanicki and Trojanowicz in *Analytica Chimica Acta* 87 411–417 (1976), that a teflon/graphite substrate produces reference electrode with drift comparable to defined electrochemical systems. Thus, although the emphasis has been on pastes, gels, dried gels, etc., to stabilize performance, there is at least this one indication to support the present inventors' observations that effective hydrophobization of a carbon substrate will result in reference electrode stability. The present inventors, however, arrive at their hydrophobic procedure not by a physical mixing of a hydrophobic material (e.g. teflon) with carbon, as done by Ruzicka and Lamm, U.S. Pat. No. 3,926,764, but by chemicaly treating the carbon to render the surface hydrophobic.

SUMMARY OF THE INVENTION

It is, therefore, a general object of the present invention to provide a solid state graphite electrode that is treated to hydrophobize the outer surface thereof, to provide an electrode that is stable and essentially free from drift.

It is another object of the present invention to provide a basic solid state graphite electrode that can be conveniently processed for use as an ion-selective electrode and as an external reference electrode for use in measuring ionic specie concentration in a test solution.

It is another object of the present invention to provide a solid state graphite electrode that requires only a coating of a graphite conductor with a silanizing agent to effectively hydrophobize the electrode surface. To produce an electrode that can operate without prior conditioning, is immediately reliable, is not subject to a drift in potential with time, and can be manufactured using mass production methods from inexpensive materials.

In accordance with the above objects, the present invention of a solid state graphite electrode provides, as the preferred electrode conductor, a supported section of graphite or a chemically and electrically like material, that is, in turn, connected electrically to a device for measuring and displaying a difference in electrical potential (emf). The graphite electrode of the present invention can be used as a reference or external electrode and can be treated further for use as an internal reference electrode in an ion-selective electrode.

The basic electrode configuration of the present invention involves coating a supported graphite conductor surface with an organic liquid, preferably a silanizing agent, to provide a covalent bonding with the hydroxyl (OH) groups on that graphite surface, rendering that surface hydrophobic.

In the electrode of the present invention, a body of a hydrophobized electrically conductive graphite material is the basis for an electrochemically active system that is sensitive to an ionic specie in solution. The electrode of the present invention rather than containing the water soluble compounds of earlier electrodes, demonstrates that the metal-salt hydrophilic layer heretofore set out as necessary for a redox coupling can be dispensed with for both ion-selective and reference electrodes. For the ion-selective or analytical electrode, the basic electrode need only be coated with a hydrophobic membrane containing a chemical ion sensor. this produces an electrode that does not require pre-treatment prior to use, exhibits a long shelf life as compared to earlier electrodes, does not drift appreciably with time, and is inexpensive to manufacture.

BRIEF DESCRIPTION OF THE DRAWINGS

In the drawings illustrate that which is presently regarded as the best mode for carrying out the invention.

DETAILED DESCRIPTION

Figure 1:
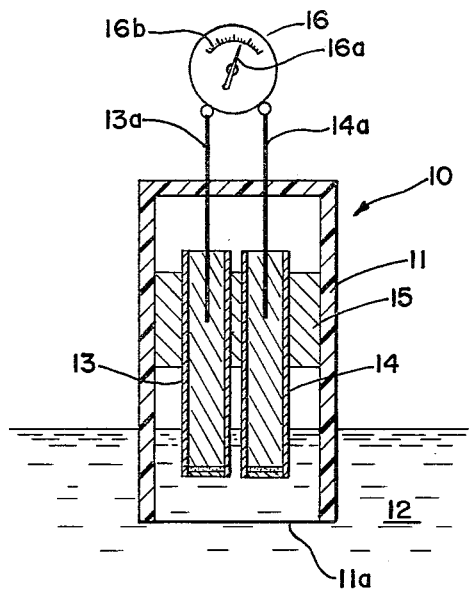
FIG. 1 is a cross-sectional view of an electrochemical probe system consisting of a basic graphite solid state external reference electrode and an ion-selective electrode of the present invention, with sensor ends shown immersed in a test solution and the opposite ends attached to a potentiometric device.

Referring now to the drawings:

In FIG. 1, as shown in a cross sectional view, is a probe assembly 10 that incorporates the electrode of the present invention and includes a housing 11 that is open at one end 11a. The housing open end is shown immersed in a test solution 12 that contains an ion-specie in solution whose concentration is to be measured. Shown in FIG. 1, the probe 10 is immersed in solution 12 to a depth where electrochemically active ends of, respectively, a basic electrode used herein as an external reference electrode 13 and an ion-selective electrode 14, are covered by the test solution. The electrodes are shown fitted through a plug 15 that is positioned within housing 11 to maintain their relative positioning therein which plug is preferably formed of an electrically non-conductive material, such as a plastic. So arranged, as illustrated by a potentiometric device 16 hereinafter referred to as meter, a difference in ion concentrations of the solution will, as explained in detail later herein, be sensed as a change of the electrical potential difference or emf, between the reference and ion-selective electrodes. That potential change is displayed by an arrow 16a as it travels over a scale 16b of the meter 16 that is shown connected through wires 13a and 14a to the electrodes. Such difference or change in potential is proportional to the logarithm of the activity of the ion as described by the well-known Nikolski-Eisenman equation. The arrangement of probe 10 with electrodes 13 and 14 is only one of many possible arrangements of the electrodes of the present invention for measuring the concentrations or activity of an ion specie in solutions containing a number of ions.

Figure 2:
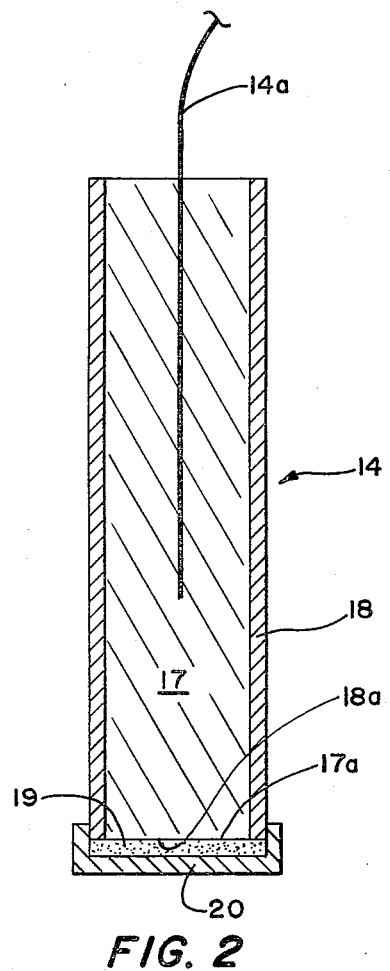
FIG. 2 is an enlarged view of one of the electrodes of FIG. 1 removed from the probe assembly.

FIG. 2 shows an enlarged sectional view of the ion-selective electrode 14 of FIG. 1, to include, as a conductor, a center rod or section 17 that is preferably formed of graphite and is supported by a non-porous, non-conductive material, shown as a glass envelope 18, the envelope electrically isolates the graphite conductor except across an electrochemically active end 17a thereof that is located in the open end 18a of envelope 18. So arranged, as set out above, wire lead 14a connects conductor 17 to meter 16. The junction of wire lead 14a in conductor 17 is preferably treated or otherwise sealed appropriately in the graphite conductor to avoid a chemical reaction therebetween that could alter the electrical conduction characteristics.

To produce electrodes to function in an ion-specific system, the graphite conductor at end 17a is coated with an organic liquid, preferably a silanizing agent 19 that provides organic molecules for covalently bonding with the hydroxyl (OH) groups on the graphite surface, rendering the graphite surface hydrophobic. So arranged, after evaporation of the silanizing agent solvent, the treated graphite electrode can be appropriately electrically connected, as set out above, for use as a reference electrode. For an ion sensitive electrode, the hydrophobized graphite is coated with a hydrophobic ion-selective membrane 20 as will be discussed in detail later herein.

THE INVENTION EVOLUTION

It is well known that graphite or carbon black is an excellent electrical conductor and is crystallized in layers wherein the carbon atoms are joined by covalent bonds with free valences at the graphite surface that can be saturated with oxygen (Ubbelohde and Lewis, *Graphite and Its Crystal Compounds*, Oxford University Press: Oxford, 1960). The degree of oxygenation of graphite affects its wettability, as for example, the adsorptive power of active charcoal, the dispersibility of ink blacks, and the vulcanization of rubber. Whereas graphite normally has excellent conductive characteristics it may be unstable as an electrode due to its surface molecules attraction to water. This has also been a problem where a metal conductor is used in solid state electrodes. As set out in the prior art portion of the present application, except for the cited work of Hulanicki and Trojanowicz, in *Analytica Chimica Acta* 87: 411–417 (1976), all earlier efforts to achieve a stable graphite electrode have involved establishing an electrochemically defined reference junction as in a chemically defined redox system, with emphasis therefore on pastes, gels, dried gels, and the like, to stablize electrode performance. The trend therefore, until the present invention, has been to achieve solid state electrode stability, by paste applications thereover along with treatment of these pastes, and the like.

That hydration is a major factor in producing electrode drift is supported by the Battaglia, et al. patent, U.S. Pat. No. 4,214,968, at Page 5, lines 31 through 37 thereof, that states:

Electrode drift is apparently due to a number of factors such as permeation of the ion-selective membrane by test solution solvent (generally water) with the passage of time, variations in ion concentration in the test solution in the region of the solution proximate the electrode, which variation is caused by the aforementioned solvent permeation, etc.

The Battaglia, et al. patent, as set out earlier herein builds on the teachings of the patent by Genshaw, et al, U.S. Pat. No. 3,856,649 that attempted to provide a practical ion-selective solid state electrode by covering an electrically conductive metal inner element with an insoluble salt having as a cation a cation form of at least a portion of the conductor element. In intimate contact with the salt is a solid hydrophilic layer that includes a water soluble salt of the anion. The cation of the insoluble salt was preferably one selected from alkali metals or alkaline earth metals and for the anion, a halogen was preferably selected. The hydrophilic layer is then covered with a hydrophobic layer to shield it from direct contact with the ion-containing solution, to avoid water adsorption thereat. The hydrophobic layer could be formed from a hydrophobic polymeric material such as PVC, thin glass, or a like material. As was set out in the Genshaw, et al. patent, it was believed, an osmotic equilibrium would be established across the hydrophobic layer similar to that established across a semi-permeable membrane, shielding the hydrophilic layer from direct contact with the ion containing solution.

The hydrophilic soluble salt containing layer was believed to be necessary as a coupling for proper electrode function in all potentiometric systems. And, of course, as the hydrophilic membrane functioned as a semi-permeable membrane, prior to use, an osmotic equilibrium needed to be established by preconditioning the electrode as by immersing the membrane in a water containing solution. A failure to precondition the Genshaw electrode or storage thereof over an extended period of time, resulted in the generation of non-Nernstian responses, the electrode exhibiting substantial random drift, and was therefore unreliable.

In an attempt to overcome the need to maintain the Genshaw, et al. patent electrode in a hydrated state and to pre-condition it, the Battaglia, et al., patent called for a drying out of the hydrophilic membrane prior to coating it with a hydrophobic ion sensor. Thereby, as set out therein, an ion-selective electrode was produced that supposedly could be used without pre-conditioning that would accurately measure specific ion concentration to demonstrate a coefficient of variation of less than about three percent (3%), and in certain highly preferred embodiments, would produce coefficients of variation of below about two percent (2%).

In practice, however, the present inventors have not found that electrodes of the Battaglia, et al. patent are initially free from drift, nor is that drift predictable, and that, with storage over time, that the electrodes become inoperable.

THE INVENTION

Figure 3:
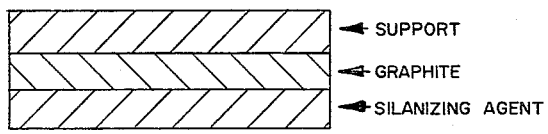
FIG. 3 is a schematic of a cross sectional view of a basic electrode configuration of the present invention.

The inventors recognizing the problem of hydration with the use of graphite as the electrode conductor, determined to stabilize that surface by coating it with an agent so as to render that surface hydrophobic but not so as to disrupt the excellent electrical conduction characteristics thereof. It was found in practice that such treated graphite conductor, as shown in the schematic of FIG. 3, would operate satisfactorily as an external reference electrode, and as such, it did not involve a humid solid water-soluble compound layer and so would not require pre-conditioning. It was also found that this electrode would exhibit a reproducible drift facilitating its calibration to allow the electrode to be used immediately, and would be stable for long periods of time.

The present inventors selected a silanizing agent as an organic liquid for coating the conductor so as to provide an organic molecule that will covalently bond with the hydroxyl (OH) group, as set out in H. P. Boehm, E.

Figure 3A:
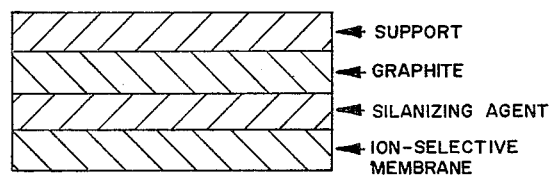
FIG. 3A is a schematic of a cross sectional view of an ion-selective electrode of the present invention.

Diehl, W. Heck, R. Sappok, Agnew *Chem. Internat.* 3: 669-677(1964), on the graphite surface to render that surface hydrophobic. The formed hydrophobic coating discourages passage of water through the graphite surface without disrupting the excellent electrical transmission characteristics thereof. For an ion-selective electrode the graphite conductor coated with a silanizing agent, after drying, is then coated with a hydrophobic membrane that has mixed therein an ion sensor, as illustrated in the schematic of FIG. 3A. While, as set out above, the present invention does not require the redox couple of the Battaglia, et al. patent and earlier patents, such can be included as shown in the schematic's of FIGS. 4 and 4A for use in measuring a specific ionic specie concentration in a redox system, or the like.

The basic electrode of the present invention, like the Genshaw, et al. and Battaglia, et al, patents involve a graphite conductor, but distinct therefrom teaches that chemically modifying the graphite surface to render it hydrophobic and does not require application of a metal-salt hydrophilic gel membrane thereto. So arranged, the hydrophobized graphite itself is capable of functioning as an external reference electrode, and needs only an application of a hydrophobic membrane containing an appropriate ion sensor therein to function as an ion-selective electrode.

In FIGS. 3 and 3A are shown cross sectional views of sandwiched layers of, respectively, the basic electrode configuration and the ion-selective electrodes as described hereinabove. Also, while the arrangements of the electrodes of FIGS. 1 through 3 shows them to be long and cylindrical in shape, such is for description only and such electrodes can be formed as chips by appropriately applying the described coatings to a sheet of graphite that is then cut into chips, the chips supported appropriately, and the electrodes electrically connected, as described, to a meter 16, or the like, to form the desired probe 10.

Schematically, the molecules of untreated graphite surface contain phenolic hydroxyl groups that would appear as:

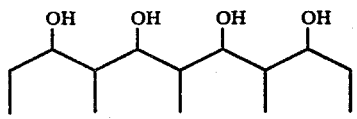

which untreated graphite surface also contains weakly acidic carboxyl groups that also provides surface hydroxl group that appears as:

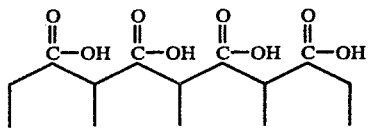

The two groups, the phenolic hydroxyl groups and the acidic Hydroxyl groups together make up about one-half of the graphite oxygen structure.

The four acidic groups that are present in graphite in approximately equivalent quantities are: (I) A more strongly acidic carboxyl group, (II) A more weakly acidic carbonyl group, (III) a phenolic hydroxyl group and (IV a carbonyl group. This fourth group (IV) has been identified as an acid chloride as set out in G. H. Heider Jr., M. B. Gelbert, A. M. Yacynych, *Analytical Chemistry* 54: 322-324 (1982). All of these acidic groups will react with silanizing agents, thereby rendering the surface of the graphite hydrophobic. With application of a silanizing agent that consists of a single or a compound of silanes will produce, in the phenolic hydroxyl groups:

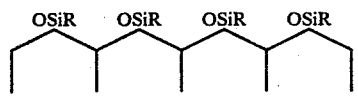

where R is a molecule composed of only carbon and hydrogen.

A silane is a group of compounds that are similar to hydrocarbons except that a tetravalent silicon replaces a carbon atom; as: $SiH_4$—monosilane, silicomethane; $Si_2H_6$—disilane, silicoethane; $Si_3H_8$—trisilane, silicopropane; and $Si_4H_{10}$—tetrasilane, silicobutane.

The graphite conductor surface after silanization is dried appropriately, either in an oven for approximately one (1) hour at a low temperature of approximately one hundred degrees Centegrade (100° C.), or in air as needed. For the ion selective electrode, the dried silanized graphite surface is coated with a hydrophobic membrane material wherein has been mixed the ion sensor, as, for example, for a $Ca^{2+}$ sensor, a calcium salt of di[p-(1,1,3,3-tetramethylbutyl)]phenyl phosphoric acid t-HDOPP set out in a U.S. patent by the present inventors, U.S. Pat. No. 4,251,470. This material, appropriately mixed with a membrane material such as PVC forms a hydrophobic ion-selective membrane. Where PVC represents the salt of the ion sensor mixed with the membrane material PVC, the structure would appear as follows:

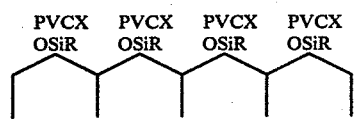

As shown above, the ion-selective membrane, PVCX, covers the silanized graphite surface but does not interact with it.

Internal reference electrodes exhibit a fixed potential that is necessary to achieve useful results. Heretofore, such electrodes have commonly been classified as:

(1) metal/metal-salt electrodes; and
(2) redox couple electrodes

Such metal/metal-salt and redox couple electrodes commonly involve a metal in contact with an insoluble salt of the metal which is in turn in contact with an electrolyte. The electrolyte, contains an anion of the metal salt. Earlier internal reference electrodes, such as the cited Battaglia, et al. patent and the Gensahw, et al. patent additionally involve an ion-selective membrane covering the metal/metal-salt or redox couple layers that coat a conductor/support. Functionally in such an electrode, electrical conductivity is provided between the metal/metal-salt by the anion.

Figure 4:
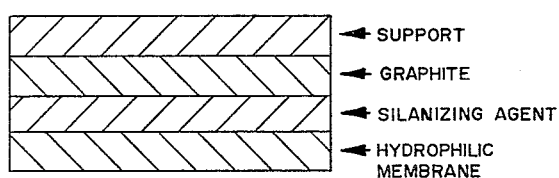
FIG. 4 is a schematic of the basic electrode of FIG. 3 further including a hydrophilic membrane applied thereto.
Figure 4A:
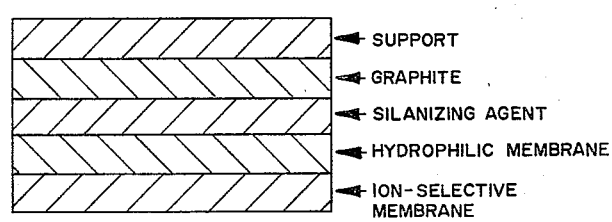
FIG. 4A is a schematic of the ion-selective or analytical electrode of FIG. 3, including a hydrophilic layer therewith.

Of course, as shown in FIGS. 4 and 4A, the basic electrode of the present invention like earlier electrodes can include the hydrophilic layer as an electrolyte but such is not functionally necessary to its operation as set out hereinabove as an internal reference electrode.

In practice, a preferred silanizing agent consists of 0.2 ml trimethylchlorosilane $(CH_3)_3SiCl$ and 0.4 ml hexamethyldisilane $(CH_3)_3SiNHNSi(CH_3)_3$, in 2.0 ml of chloronaphthalene (ClNap). This solution was used as the silanizing agent for treating the graphite electrodes of the present invention, which electrodes were then tested as set out hereinbelow. However, it should be understood that the graphite conductor to provide the electrode of the present invention, can be coated with any like silinizing agent or like organic liquid that includes an organic molecule that will covalently bond with the graphite hydroxyl (OH) groups to render the graphite hydrophobic. Therefore, while the above silanizing agent has been successfully used in practice, any silanizing agent, or the like, could be used successfully to produce the electrodes of the present invention and a list of a number of such silanizing agents is listed later herein.

PREPARATION OF THE ELECTRODE

Heretofore solid-state electrodes that utilize a wire conductor have commonly been manufactured by successive dipping of that wire sequentially into generally viscous solutions of the component layers of the individual finished electrode to construct a bulbous multilayer "solid-state" electrode. Alternatively, such electrodes have included covering the conductive wire tip with individual layers of an ion-selective glass. With either of these procedures, a resulting ion-selective membrane and even the layers thereunder will be of relatively non-uniform thickness presenting varying conductivity therethrough as between supposedly identical electrodes. More recently, as set out in the above cited Battaglia, et al. and Genshaw, et al., patents and in the earlier cited patent by Ruzicka, et al., electrode layers have preferably been pressed together, or by otherwise applying one layer over another in a planar or substantially planar configuration. Preferably if the electrode of the present invention is prepared on a pliant support, it may be configured into any useful geometry by cutting, bending, or the like, to permit contact of the ion-selective membrane with a test solution.

Figure 5:
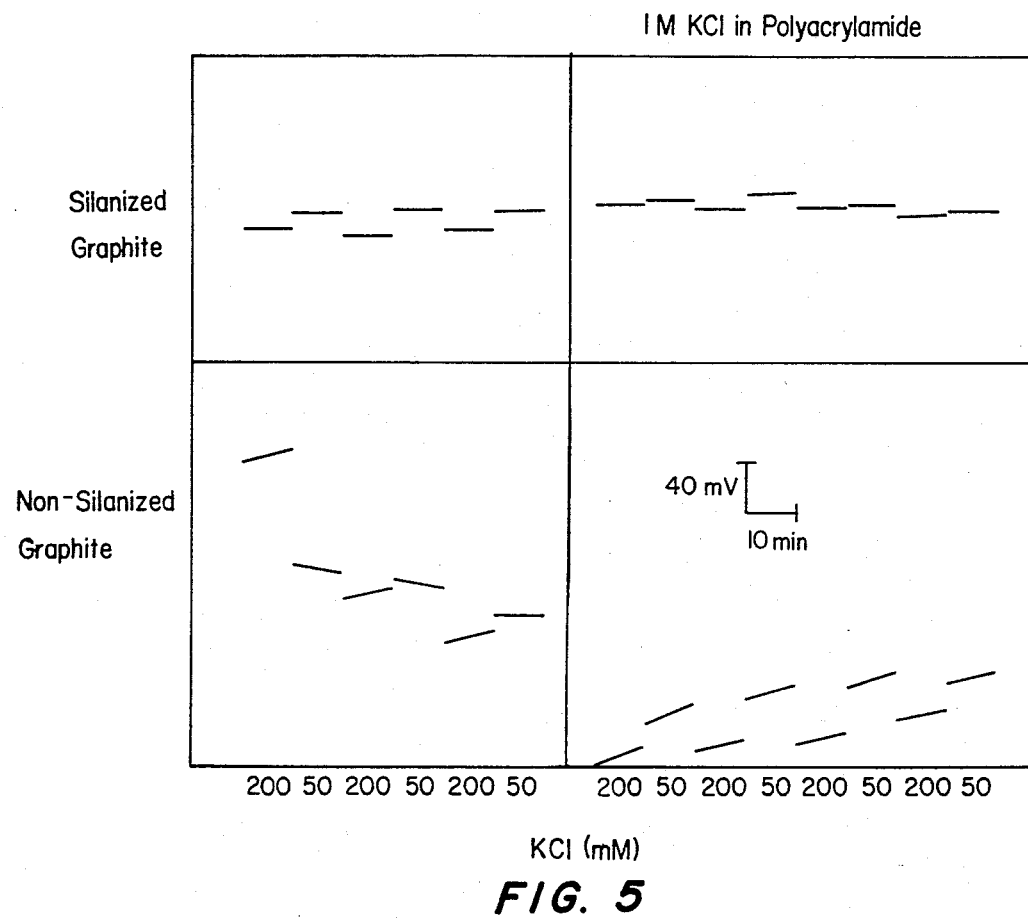
FIG. 5 is a graph a comparing the function of silanized and non-silanized graphite ion-selective electrodes measuring $Ca^{2+}$ in varied concentrations of KCl.
Figure 6:
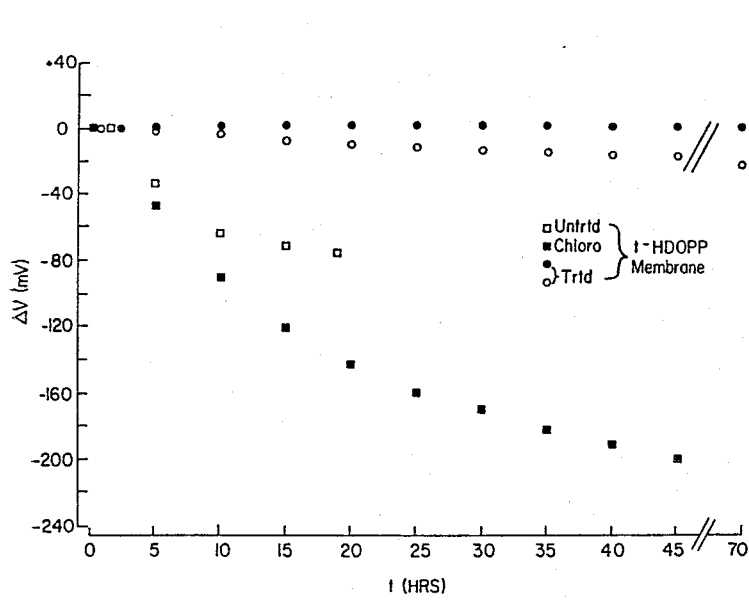
FIG. 6 is a graph showing a comparison of drift with time for treated and untreated graphite ion-selective electrodes.
Figure 7:
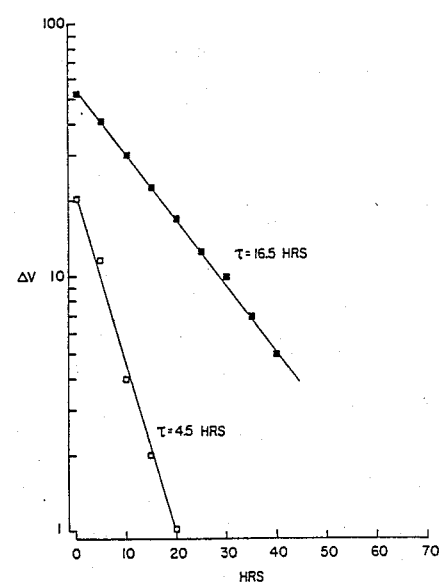
FIG. 7 is a graph of untreated graphite and chloronapthalene treated graphite electrode drift over time.

As set out hereinabove, the present invention is directed to a graphite conductor with free valences available at the surface that can be saturated with oxygen. In practice, the electrodes that were constructed and used as set out in Examples 1 and 2 hereinbelow that refer to FIGS. 5 and 6, utilized cylindrical graphite. Use of various sources and grades of graphite was found not to be a factor in electrode performance. Rather, silanization was the critical variable, as illustrated in Example 3 that refers to FIG. 7. Here a non-silanized graphite conductor was utilized, and as shown performed unsatisfactorily as an electrode, drifting with a time constant of approximately 4.5 hours. Also shown therein, an electrode treated with the organic solvent, a chloronapthalene electrode, drifted with a time constant of 16.5 hrs. This result was surprising since the earlier literature had indicated that treatment of graphite with other organic materials (e.g. benzene) tended to make more stable reference electrodes (J. Ruzicka and C. G. Lamm, *Analytica Chimica Acta*: 53: 206–208 (1971). The consistent results of Examples 1 and 2, FIGS. 5 and 6, illustrate the utility of graphite treated as described with a silanizing agent, rendering that graphite surface hydrophobic. Whereas, regardless of the graphite purity, as illustrated in FIG. 7, without so treating the graphite surface, it will not perform satisfactorily as an electrode. In practice, it was also found that glassy carbon, an expensive derivative of graphite, when untreated, also showed considerable drift as an electrode but the drift improved substantially when given the silanization treatment.

The graphite conductor is connected to an appropriate wire lead for conducting a voltage therethrough to a meter 16 and is supported such as by fitting a cylindrical section of graphite within a non-conductive glass sheath that is open at both ends. So arranged, one end of the graphite cylinder receives a wire lead implated therein. The opposite exposed graphite end that is for immersion in a test solution is coated as set about above, with a silanizing solution. The silanizing agent provides a covalent bonding to the hydroxyl (OH) groups on the graphite surface, rendering that surface hydrophobic without a disruption of the excellent electrical conduction characteristics of that graphite. So prepared, this basic non-metallic electrode consists of a supported section of graphite electrically connected to a wire lead and has its electrochemically active end surface coated with a silanizing agent, forming after that silanizing agent layer was dried, a basic electrode. The basic electrode is immediately usable as an external reference electrode or for sensing the activity of a particular ion when used in conjunction with an ion-selective membrane.

While as set out hereinabove, test electrodes have been produced and performed satisfactorily that even utilizes pencil lead as the conductor material. A preferred manufacturing technique to fabricate a basic electrode might involve: a sheet of graphite material on a supporting base and, uniformly coating that sheet with a layer of a silanizing agent; drying that layer by baking in an oven at an appropriate heat until the layer is dry, or air drying for a period of time necessary to effect a uniformly dried surface. Thereafter, to fabricate an ion-selective electrode and/or internal reference electrode, as set out herein below, additional layers can be applied. After drying, the coated graphite sheet can be cut appropriately into sections and electrically connected to a wire lead.

For an ion-selective electrode the above described basic electrode electrochemically active end is coated, capped or otherwise has fixed thereto, a hydrophobic membrane material wherein is uniformly mixed a an ion sensor, ion carrier or exchange for the ionic specie to be sensed. Suitable membrane materials for coating, the silanized graphite surface may involve any of the hydrophobic natural or synthetic polymers that are capable of forming or being formed into a thin film over the treated graphite surface that is of sufficient permeability to produce, in combination with the selected ion sensor apparent ionic mobility thereacross. In practice, PVC has been utilized as the membrane material. However, it should be understood that other polymers could be so used. As for example, vinylidene chloride, acrylonitrile, polyurethanes (particularly aromatic polyurethanes), copolymers of polyvinyl chloride and polyvinylidene chloride, polyvinyl butyral, polyvinyl formal, polyvinylacetate, silicone elastomers, and copolymers of polyvinyl alcohol, cellulose esters, polycarbonates, carboxylated polymers of polyvinyl chloride and mixtures and copolymers of such materials. Films of such materials which include the ion sensors and as appropriate, carrier solvents may be prepared using conventional film coating or casting techniques and may be formed either by coating and film formation directly over the treated graphite surface, or by separate formation and lamination thereto.

As set out hereinabove, the membrane includes an ion sensor mixed therein appropriate to provide selected ion specie sensing. Such an ion sensor is generally a substance capable of selectively associating or binding itself preferentially to a desired specific alkali metal, alkaline earth cation or the like. The selectivity of the electrode for a particular ion-specie is due to the chemical nature of the ion sensor and thus, the use of different chemical components as the ion sensor will provide different membranes and thus, different ion-selective electrodes. A large number of chemical components are available, their use only limited to the components solubility in an organic solvent and in the membrane material. Further, additional to the described mix of a polymer and a chemical component as the ion selective membrane, an ion sensitive glass could also be employed. As for example, a sodium sensitive glass is available from Corning Company identified as NAS 11-18, that is suited for such utilization.

The basic electrode of the present invention as illustrated in the schematic of FIG. 3 can therefore be arranged as the ion-selective electrode of FIG. 3A by application of the above described membrane material that has mixed thereon a selected chemical component. As for example: for a calcium ($Ca^{2+}$) sensitive electrode, a calcium salt of di[p-(1,1,3,3-tetramethylbutyl)-phenyl]phosphoric acid has been utilized; for a potassium ($K^+$) sensitive electrode valinomycin was selected as the chemical component; for a sodium ($Na^+$) sensitive electrode Corning NAS sodium sensitive glass or Flucka Chemical Co. ETH 227 was used as the chemical component. The above illustrates only a few of the many possible electrode arrangements and should be understood are here presented as examples only and not as limitations to the invention.

Also, it should be understood that with appropriate selection of the membrane material and chemical components for mixing therein the basic electrode can also be arranged for use for detecting gas concentrations and pH. For example, a pH sensor can be produced by mixing of one of a number of hydrogen-sensitive organic molecules such as quinhydrone, p-octadecyloxy-m-chlorophenylhydrazone mesoxalonitrile (III) (OCPH) or tridodecylamine (TDDA) with the membrane material for application, as described, to the basic electrode. Such pH sensors will be functionally comparable to a conventional expensive glass pH electrode, but can be produced at appreciably less cost. Similarly, for a carbon dioxide electrode, starting with the above pH sensor, a bicarbonate buffer solution is maintained so as to cover over the electrode membrane surface by application of a gas permeable membrane thereover, such as a polypropylene, copolymers of polycarbonate or teflon. So arranged, changes in pH of the bicarbonate buffer solution will represent changes in carbon dioxide concentration of the sensed solution.

Above are only a few of the many possible arrangements where the basic electrode is configured for sensing ionic-specie and certain gas concentrations, and should be understood are presented for example only and not as limitations.

As set out hereinabove, the basic electrode shown in FIG. 3 can be configured like the external reference electrode shown schematically in FIG. 4 or like the ion-selective internal reference electrode of FIG. 4A by addition of a hydrophilic layer over the hydrophobized graphite surface, wherein are suspended pairs of the same chemical species, usually as ions, that are in differing oxidation states. Such is, of course, a redox couple. Such electrodes would thereby be appropriate for utilization in a reduction-oxidation system.

Such hydrophilic layer can be a selected water permeable matrices of a hydrophilic colloid such as gelatin, polyvinyl alcohol, polyacrylamide, polyvinyl pyrolidone, or the like, which colloid is preferably: sufficiently hardened or cross-linked to prevent substantial dissolution thereof by water; and is sufficiently hydrophilic to permit electrolytic contact with the conductor. The present invention for most functions would not incorporate the above described hydrophilic layer to the silanized graphite conductor surface. However, such inclusion should, of course, be understood would be within the scope of the present disclosure.

As set out numerous times hereinbefore, the basic electrode and adaptations thereof, as shown in FIGS. 3 and 3A, includes covering an electrochemically active portion of a graphite conductor with an organic liquid, preferably a silanizing agent, that provides a covalent bonding with the hydroxyl (OH) group on that graphite surface, rendering that surface hydrophobic. The basic mechanisms involved in silanizing a graphite surface are shown as:

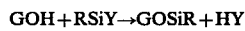

where "G" denotes graphite, "Y" denotes a material bonded to a silane to form a derivative and the "R" of the "RSiY" denotes a wide variety of possible types of silanizing agents. In practice, a silanizing solution consisting of 0.4 ml hexamethyldis alazane [$(CH_3)_3$ SiNH-Si$(CH_3)_3$] and 0.2 ml trimethylchlorosilane [$(CH_3)_3SiCl$] in 2.0 ml of chloronapthalene was utilized successfully as the silanizing agent. Additionally, for use as described above, herinbelow are listed other silanizing agents that can be used in the present invention:

Allyldimethylchlorosilane, ADMCS,
Allyltrimethylsilane,
3-Aminopropyltriethoxysilane,
Benzyltrichlorosilane,
1,3-Bis(chloromethyl)-1,1,3,3-tetramethyldisilazane,
N,O-Bis(trimethylsilyl)acetamide, BSA,
Bis(trimethylsilyl)acetylene),
N,O-Bis(trimethylsilyl)carbamate, BSC,
N,N-Bis(trimethylsilyl)formamide, BSF,
N,N-Bis(trimethylsilyl)methylamine,
Bis(trimethylsilylmethyl)mercury,
N,O-Bis(trimethylsilyl)trifluoroacetamide, BSTFA,
N,O-Bis(trimethylsilyl)trifluoroacetamide,
N,N'-Bis(trimethylsilyl)urea,
tert-Butyldimethylchlorosilane, TBDMSCI,
tert-Butyldiphenylchlorosilane,
tert-Butyltrimethylsilylacetate,
Chloromethyldimethylchlorosilane, CMDMCS,
Chloromethyltrimethylsilane,
3-Chloropropylmethyldichlorosilane,
Diethyldichlorosilane,
Dimethylchlorosilane, DMCS,
Dimethyldichlorosilane,
Dimethyldiethoxysilane,
Dimethyldiethoxysilane,
Diphenyldichlorosilane,
Ethyltrichlorosilane,
Ethyltriethoxysilane,
Ethyl trimethylsilylacetate, ETSA,
Hexamethyldisilane, Hexamethyldisilazane, HMDS,
Hexamethyldisiloxane, HMDSO,
Hexamethyldisilthiane,
Iodotrimethylsiane,
Methylthiotrimethylsilane,
Methyltrichlorosilane,
Methyltriethoxysilane,
N-Methyl-N-trimethylsilylacetamide, MSA,
N-Methyl-N-trimethylsilyltrifluoroacetamide, MSTFA,
Methylvinyldichlorosilane,
Octamethylcycloterasiloxane,
Pentafluorophenyldimethylchlorosilane,
Phenyldimethylchlorosilane,
Phenylselenomethyltrimethylsilane,
Phenyltrichlorosilane,
Polymethylhydrogensiloxane, PMHS,
Silicon tetrachloride,
Sodium bis(trimethylsilyl)amide,
Tetraethoxysilane,
Tetramethoxysilane,
1,1,3,3-Tetramethyldisilazane, TMDS,
Tetramethylsilane, TMS,
Trichlorosilane,
Triethylchlorosilane,
Triethylsilane,
Trimethylbromosilane, TMB,
Trimethylchlorosilane, TMCS,
Trimethylethoxysilane,
N-Trimethylsilylacetamide,
Trimethylsilylazide, TMSA,
Trimethylsilyl chlorosulfonate,
Trimethylsilylcyanide,
N-Trimethylsilyldiethylamine, TMSDEA,
N-Trimethylsilyldimethylamine, TMSDMA,
N-Trimethylsilylimidazole, TMSI,
Trimethylsilylisothiocyanate,
Trimethylsilyl methanesulfonate,
3-(Trimethylsilyl)-1-propanesulfonic acid sodium salt, DSS,
Trimethylsilyl trifluoromethanesulfonate,
Triphenylchlorosilane,
Triphenylsilane,
Triphenylsilanol,
Vinyltrichlorosilane,
Vinyltriethoxysilane,
Vinyltrimethylsilane,
Vinyl-tris(2-methoxyethoxy)silane.

Hereinabove has been set out a preferred structure and utilization of the basic electrode and derivatives thereof of the present invention. The following are examples of the actual construction of electrodes of the invention and their utility that are here presented to demonstrate the functioning thereof. Each example 1, 2 and 3 relate respectively, to FIGS. 5, 6 and 7 as set out therein.

EXAMPLE 1

Tests of silanized graphite for use as an external reference electrode were conducted and the results are shown in FIG. 5. Shown therein, four different treatments of the reference electrode are illustrated in top left, top right, lower left and lower right quadrants. In all four cases, the external reference electrode was run against a calcium ion-selective electrode made by coating a silanized graphite internal reference electrode with t-HDOPP embedded in PVC. The two electrodes, identified as external reference and ion-selective, were both dipped into a solution with constant calcium chloride concentration, (one millimolar) and at different potassium chloride concentration concentrations, e.g. 50 millimolar or 200 millimolar. The purpose of the test was to demonstrate the stability of the external reference electrode to varying concentrations of chloride or ionic strength.

FIG. 5, lower left, shows the effect of untreated or non-silanized graphite as the external electrode. As shown, there is both a considerable offset potential between the various potassium concentrations and a large drift in each solution.

FIG. 5, lower right, shows that by adding a layer of an electrolyte of 1 M KCl embedded in a hydrophilic plastic membrane of polyacrylamide, that the offset and the drift remain but are now more "predictable".

FIG. 5, upper left, demonstrates the effect of silanizing graphite. Shown thereon, the offset due to ionic strength or chloride concentration is reduced and the drift is essentially reduced to zero.

FIG. 5, upper right, exemplifies the effect of the hydrophilic polyacylamide membrane with the 1 M KCl solution that reduces the offset seen between the two electrodes in the various potassium chloride solutions. The overall drift is essentially the same as upper left.

EXAMPLE 2

This example relates to FIG. 6 that shows a comparison of long-term drift of $Ca^{2+}$ ion-selective electrodes t-HDOPP with untreated internal graphite reference electrodes (□), graphite electrodes treated with the organic solvent chlorona pthalene (■) and silanized graphite electrodes (o) and (●). Shown therein, untreated $Ca^{2+}$ electrodes (□) display considerable drift (80 mV) in a 20 hour period. Pre-treating the graphite electrode (■) with the organic solvent chloronapthalene augments the rate of drift (130 mV/20 hr). The circles (o) and (●), represent the range of drift experienced among $Ca^{2+}$ t-HDOPP electrodes pre-treated with the preferred silanizing agents hexamethyldisilazane and trimethylchlorosilane in the organic solvent chloronapthalene. In the worst case, (o) drift was linear and was at the rate of −0.25 mV/hour and in the best case, (●) drift was random and did not exceed 0.1 mV.

EXAMPLE 3

This example relates to FIG. 7 that shows drift plotted on semi-logarithm coordinates for untreated graphite (□) and graphite treated with chloronaphthalene (■). The drift for both is shown to be exponential and yields time constants of 4.5 and 16.5 hours, respectively. This contrasts with graphite treated with silanes which show a more linear drift characteristics with time, as illustrated in FIG. 6.

The present invention as set out herein in its most basic form is an electrode that includes a graphite conductor whose surface is coated with an organic liquid; preferably a silanizing agent, to provide a covalent bonding with the hydroxyl (OH) groups on that graphite surface, rendering that surface hydrophobic, and includes electrically connecting that conductor to a potentiometric device. This basic electrode can then be further arranged, as set out herein to provide an ion-selective electrode capable of sensing ionic activity of a specific ion-specie, and can optionally include a hydrophilic membrane with a redox couple for arrangement as an internal reference electrode, and the like.

While a number of preferred electrodes of the present invention have been shown and described herein, it should be understood that the present disclosure is made by way of example only and that other arrangements of the basic electrode additional to those shown herein and their use are possible without departing from the subject matter coming within the scope of the following claims, which claims we regard as our invention.

We claim:

1. An electrode for use in making potentiometric measurements comprising,
    a graphite conductor;
    means supporting said graphite conductor;
    means for electrically connecting said graphite conductor to a means for sensing a difference in electrical potential between the electrode and a reference source; and
    an organic liquid coating said graphite surface and chemically bonding therewith so as to render that surface hydrophobic.

2. An electrode as recited in claim 1, wherein,
    the organic liquid is a silanizing agent.

3. An electrode as recited in claim 2, wherein,
    the silanizing agent is a solution containing approximately a 2:1 ratio of hexamethyldisilazane and trimethylchlorosilane in chloronapthalene.

4. An electrode as recited in claim 1, further including,
    ion-selective membrane for arrangement over the hydrophobized graphite surface after drying thereof arranged for sensing an ionic-specie therein.

5. An electrode as recited in claim 4, wherein,
    the ion-selective membrane is a polymeric material wherein is mixed an ion sensor for the ionic-specie to be measured.

6. An electrode as recited in claim 5, wherein,
    the ion-selective polymeric material is polyvinylchloride (PVC).

7. An electrode as recited in claim 4, wherein,
    the ion-selective membrane is a glass that is ion-selective.

8. An electrode as recited in claim 4, further including,
    a hydrophilic layer containing pairs of a same chemical specie that are in differing oxidation states that is applied to the hydrophobized graphite surface.

9. An electrode as recited in claim 8, further including,
    application of an ion-selective membrane over said hydrophilic layer; and
    connection of said electrode as an internal reference ion-selective electrode to a potentiometer device.

10. An electrode as recited in claim 9, wherein,
    the ion-selective membrane is a polymeric material.

11. An electrode as recited in claim 10, wherein,
    the ion-selective polymeric material is a polyvinylchloride (PVC).

12. An electrode as recited in claim 1, wherein,
    the means supporting said graphite conductor is a glass envelope.

13. An electrode as recited in claim 1, wherein,
    the means supporting said graphite conductor is an envelope formed from a polymeric material.

14. An electrode as recited in claim 1, wherein,
    the graphite conductor is formed from a compound of graphite and other conductive and non-conductive materials.

15. An ion-selective electrode for use in making potentiometric measurements comprising,
    a graphite conductor;
    means supporting said graphite conductor;
    means for connecting said graphite conductor to a means for sensing a difference in electrical potential between the electrode and a reference source;
    an organic liquid coating said graphite surface and chemically bonding therewith to render that surface hydrophobic; and
    an ion-selective membrane applied over said organic liquid coated graphite surface for sensing an ionic-specie therein.

16. An ion-selective electrode as recited in claim 15, wherein,
    The ion-selective membrane is a polymeric material.

17. An ion-selective electrode as recited in claim 16, wherein,
    the polymeric material is polyvinylchloride (PVC).

18. An ion-selective electrode as recited in claim 17, wherein,
    a salt of the ionic-specie to be sensed is mixed in the polymeric material.

19. An ion-selective electrode as recited in claim 15, wherein,
    the ion-selective membrane is a glass that is ionic-specie selective.

20. An ion-selective electrode as recited in claim 15, wherein,
    the organic liquid coating is dried prior to application of the ion-selective membrane thereover.

21. An ion-selective electrode as recited in claim 15, wherein,
    the organic liquid is a silanizing agent.

22. An ion-selective electrode as recited in claim 21, wherein,
    the silanizing agent is a solution containing approximately a 2:1 ratio of hexamethyldisilazane and trimethylchlorosilane in chloronapthalene.

23. An ion-selective electrode as recited in claim 15, wherein,
    the means for supporting said graphite conductor is a glass envelope.

24. An ion-selective electrode as recited in claim 15, wherein,
    the means supporting said graphite conductor is an envelope formed from a polymeric material.

25. An ion-selective electrode as recited in claim 15, wherein,
    the graphite conductor is formed from a compound of graphite and other conductive and non-conductive materials.

26. An ion-selective electrode as recited in claim 15, wherein,
    the ion-selective membrane is gas permeable; and a bicarbonate buffer solution is arranged between said ion-selective membrane and the hydrophobized graphite conductor.

27. An ion-selective electrode as recited in claim 26, wherein,
    the ion-selective membrane is a polymeric material.

28. An ion-selective electrode as recited in claim 15, further including,
    a hydrophilic layer containing pairs of a same chemical specie that are in differing oxidation states arrranged between the hydrophobized graphite and the ion-selective membrane.

29. An ion-selective electrode as recited in claim 28, further including,
electrical connection of the electrode as an internal reference ion-selective electrode to a potentiometer device.

30. An electrode for making ion-selective measurements comprising,
a graphite conductor;
means supporting said graphite conductor;
an electrically conductive means connected to said graphite conductor; and
an organic liquid coating said graphite surface and chemically bonding therewith so as to render that surface hydrophoic.

31. An electrode as recited in claim 30, further including
an ion-selective membrane applied over said organic liquid coated graphite surface.

* * * * *